US00PP28340P2

(12) United States Plant Patent
Caprelian

(10) Patent No.: US PP28,340 P2
(45) Date of Patent: Aug. 29, 2017

(54) MC 1936

(50) Latin Name: *Prunus persica*
Varietal Denomination: MC 1936

(71) Applicant: Farmex Land Management, Inc., Sanger, CA (US)

(72) Inventor: Marvin Caprelian, Sanger, CA (US)

(73) Assignee: Farmex Land Management, Inc., Sanger, CA (US)

( * ) Notice: Subject to any disclaimer, the term of this patent is extended or adjusted under 35 U.S.C. 154(b) by 0 days.

(21) Appl. No.: 15/530,322

(22) Filed: Dec. 21, 2016

(51) Int. Cl.
*A01H 5/08* (2006.01)

(52) U.S. Cl.
USPC ..... Plt./198

(58) Field of Classification Search
USPC ..... Plt./198
See application file for complete search history.

(56) References Cited

U.S. PATENT DOCUMENTS

| | | | |
|---|---|---|---|
| PP9,438 | P | 1/1996 | Doyle |
| PP15,496 | P2 | 1/2005 | Slaughter et al. |
| PP26,901 | P2 | 7/2016 | Yakligian |

*Primary Examiner* — June Hwu
(74) *Attorney, Agent, or Firm* — Mark D. Miller

(57) ABSTRACT

A new and distinct variety of peach tree which is distinguished by producing fruit having a freestone rather than a clingstone, with the fruit ripening for harvest approximately September 7-21 in a normal year.

7 Drawing Sheets

BACKGROUND OF THE NEW VARIETY

The present invention refers to a new variety of peach tree which will hereinafter be denominated as the 'MC 1936' which produces freestone fruit which are mature for commercial harvesting and shipment approximately September 7-21 in a normal growing year in the San Joaquin Valley of Central California as a firm, late, fresh market peach with a good red blush coloration.

In the development of new commercial varieties of fruit specific characteristics places a premium on those varieties, which are early or late maturing, in the growing season. However, many such varieties have small size, lack of flavor, or coloration. In some instances there are other undesirable characteristics that decrease the commercial success. In order for a fruit to be a commercial success it must possess those characteristics of good size, good color, and good flavor. At the same time the date of maturity must be separate or different than other similar fruit. The fruit of the present variety also tends to retain its firmness longer than other peaches. This new variety meets all of the aforementioned criteria and therefore is of commercial appeal to the consumer.

ORIGIN AND ASEXUAL REPRODUCTION OF THE NEW VARIETY

A whole plant of the present variety of peach tree was discovered by the inventor in a grove of 'Fayette' peach trees (unpatented) located near Sanger, Calif. The inventor discovered it as a new tree in the year 2006 and observed it for eight years. The new variety was asexually reproduced in 2013 at Sanger, Calif. by bud grafting eight trees onto 'Nemaguard' (unpatented) rootstock in a nearby orchard. These eight trees first produced fruit in 2016. The inventor has carefully examined the asexually reproduced trees which appear to be identical to the parent.

SUMMARY OF THE NEW VARIETY

The subject 'MC 1936' variety is characterized by producing a large, firm freestone fruit which has good red blush coloration and is ripe for commercial harvesting and shipment approximately the second and third weeks of September in the San Joaquin Valley of Central California. The new variety is similar to 'Calara' (U.S. Plant Pat. No. 15,496), but from which is distinguishable in that the fruit is similar in size and appearance, has a freestone rather than a clingstone, and ripens after the end of the harvesting period of 'Autumn Flame' (U.S. Plant Pat. No. 9,438) and overlaps with the beginning of the harvesting period of 'Calara'. The fruit of this new variety is firm, and possesses a very good flavor as well as an aroma that is greatly acceptable for a late ripening variety.

BRIEF DESCRIPTION OF THE DRAWINGS

The accompanying drawings are color photographs showing fruit and foliage of the new variety.

DETAILED DESCRIPTION

Figure 1:
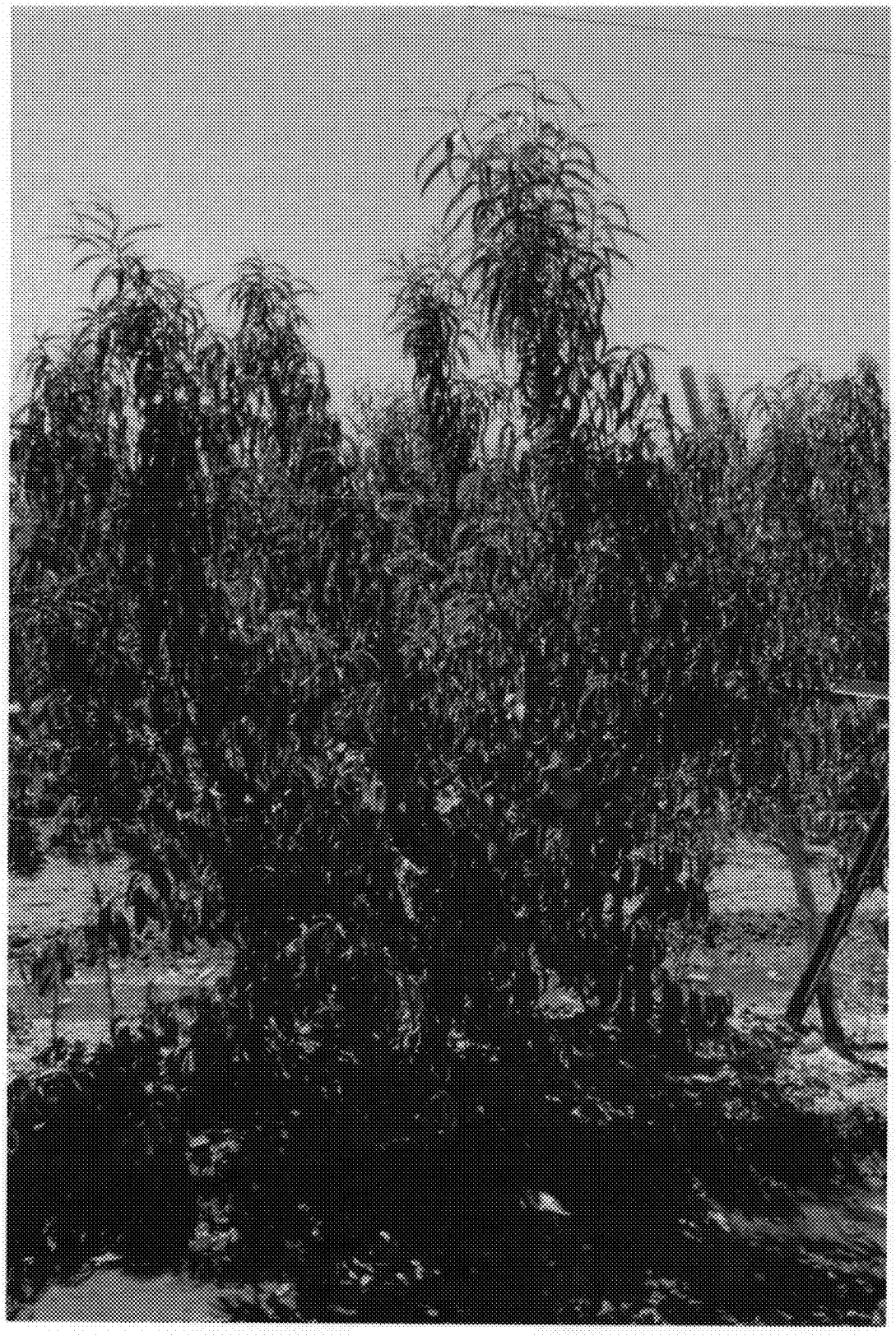
FIG. 1 shows an entire tree of the new variety including leaves, branches and fruit.
Figure 2:
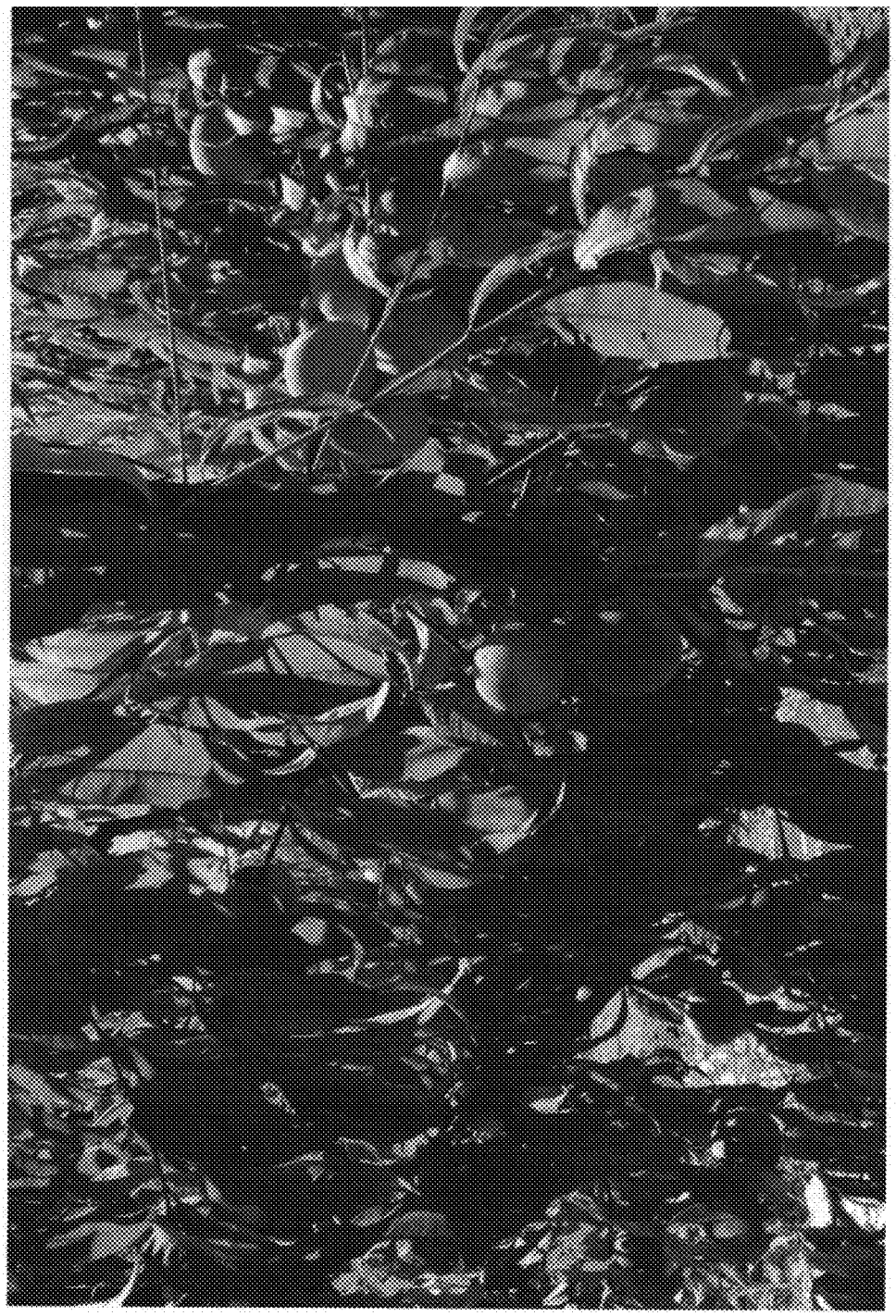
FIG. 2 shows a close up of leaves, fruit and branches of the new variety in situ.
Figure 3:
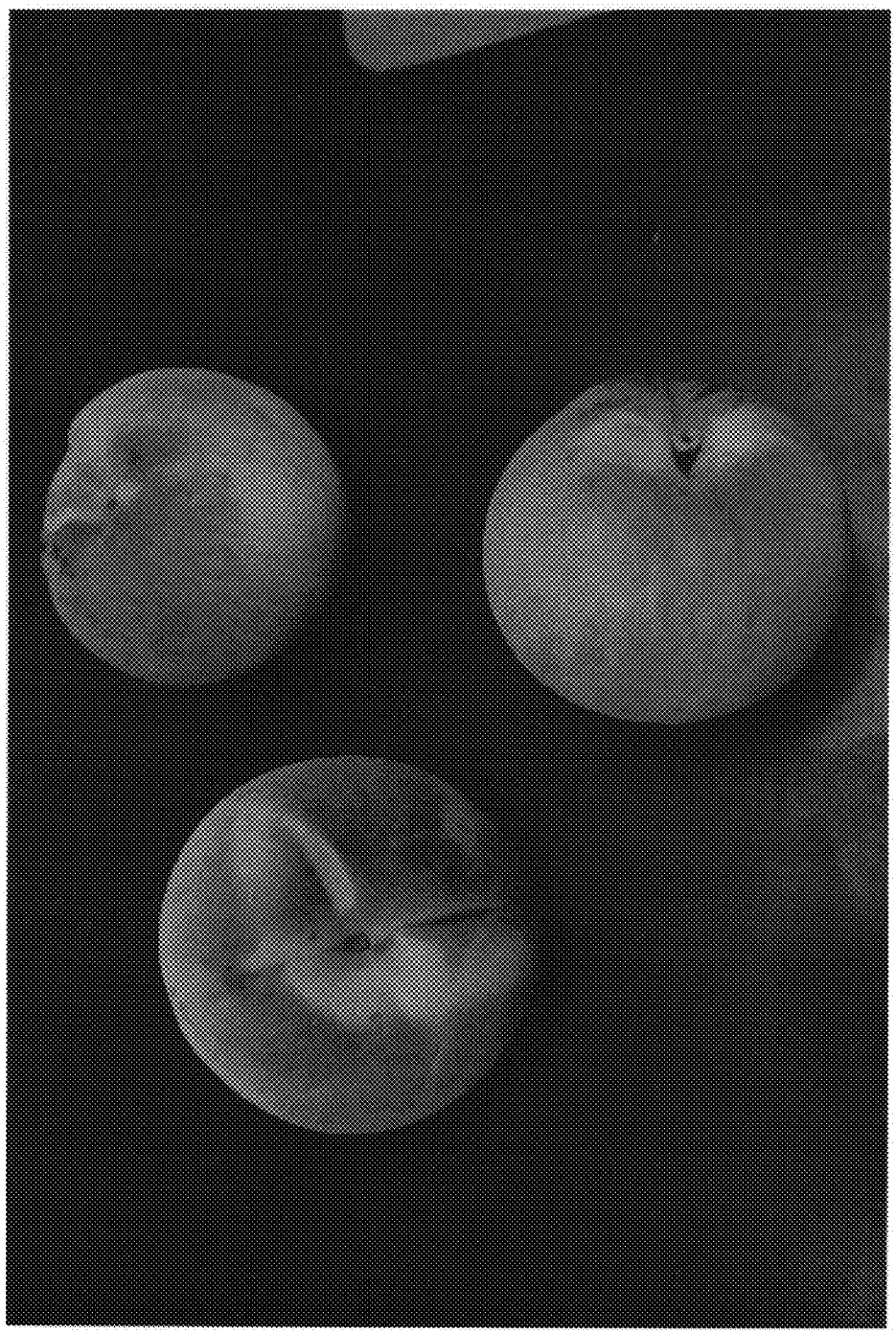
FIG. 3 shows whole uncut fruit of the new variety.
Figure 4:
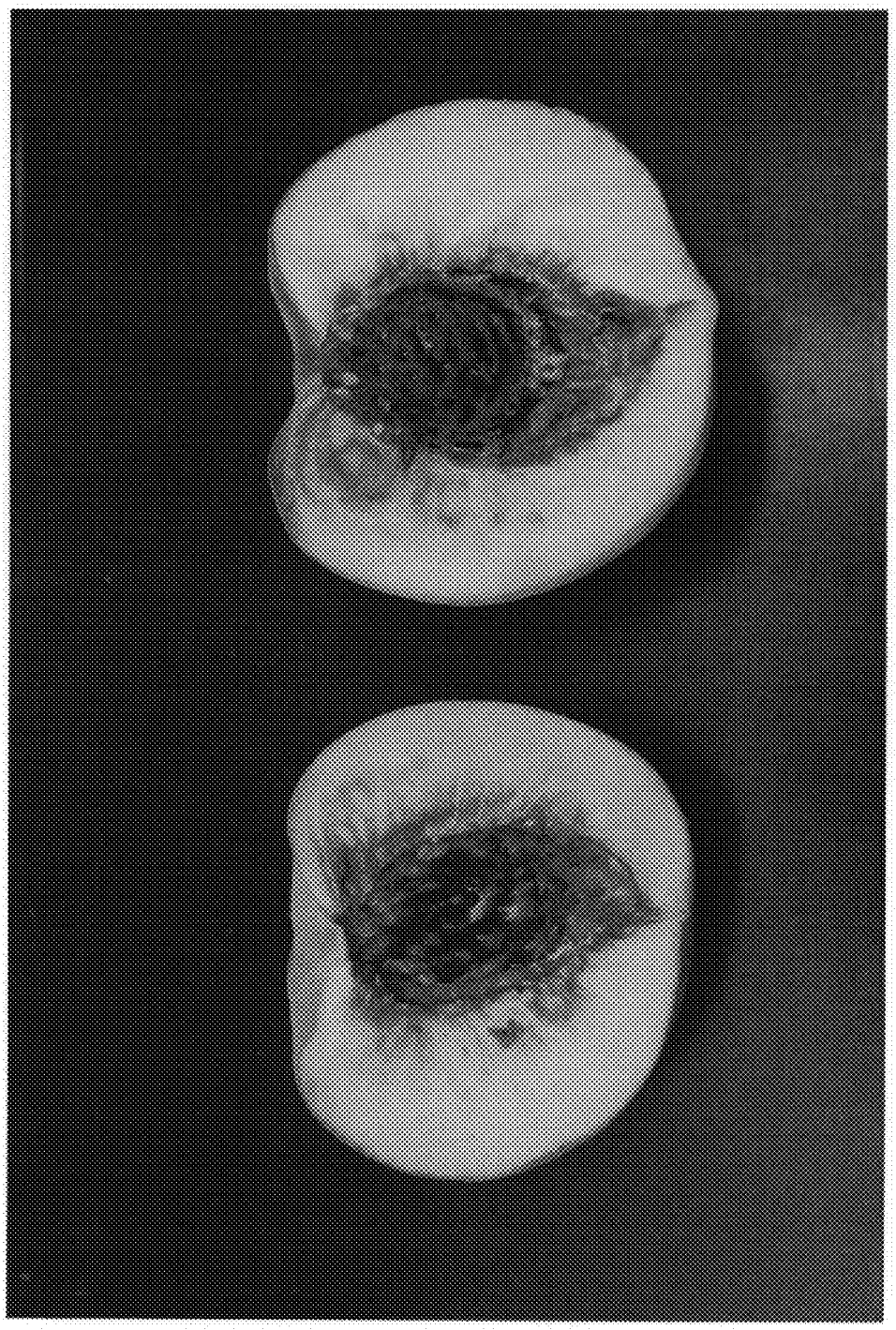
FIG. 4 shows fruit cut open showing the fruit stone (pit) and the flesh.
Figure 5:
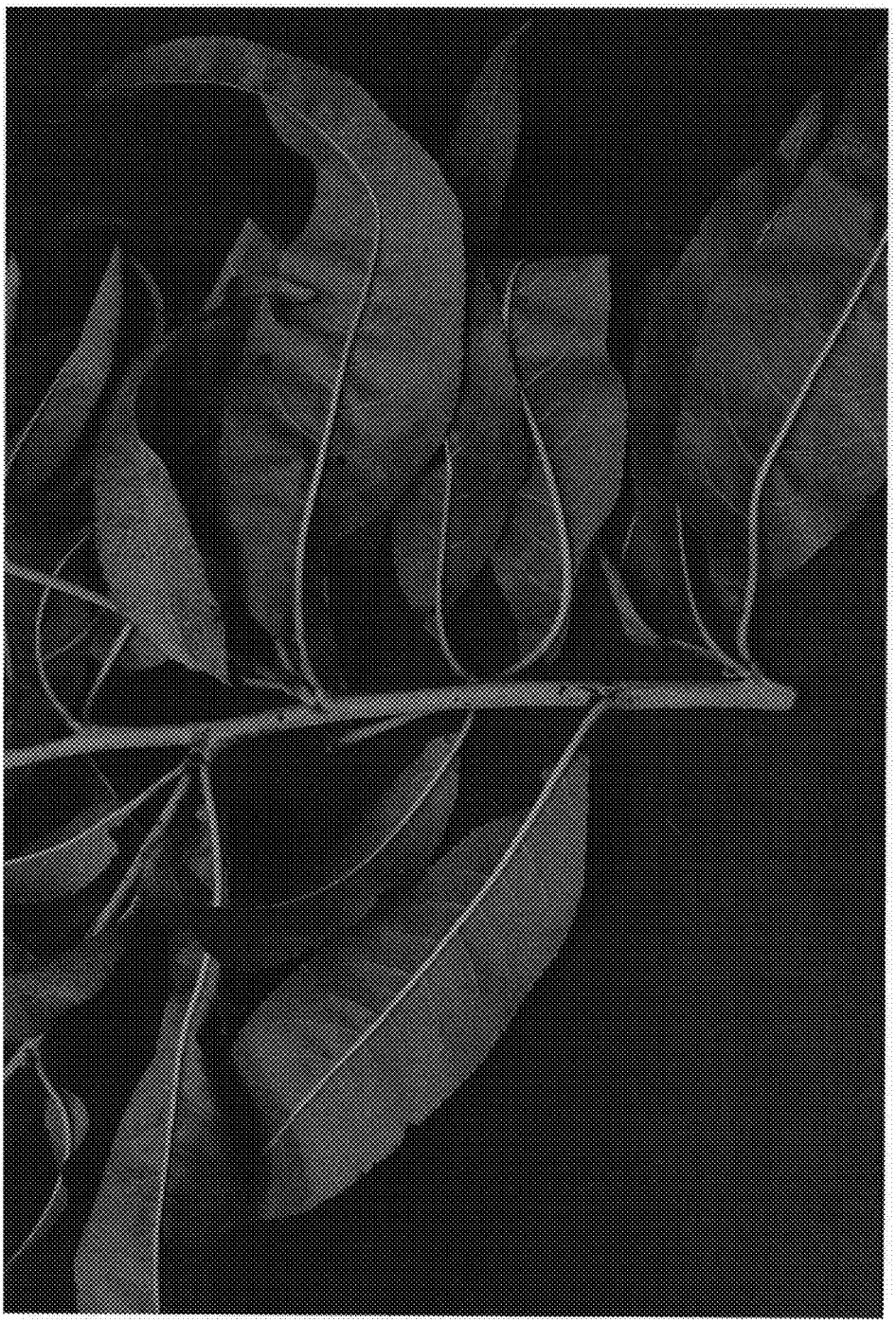
FIG. 5 shows a branch of the new variety with leaves.
Figure 6:
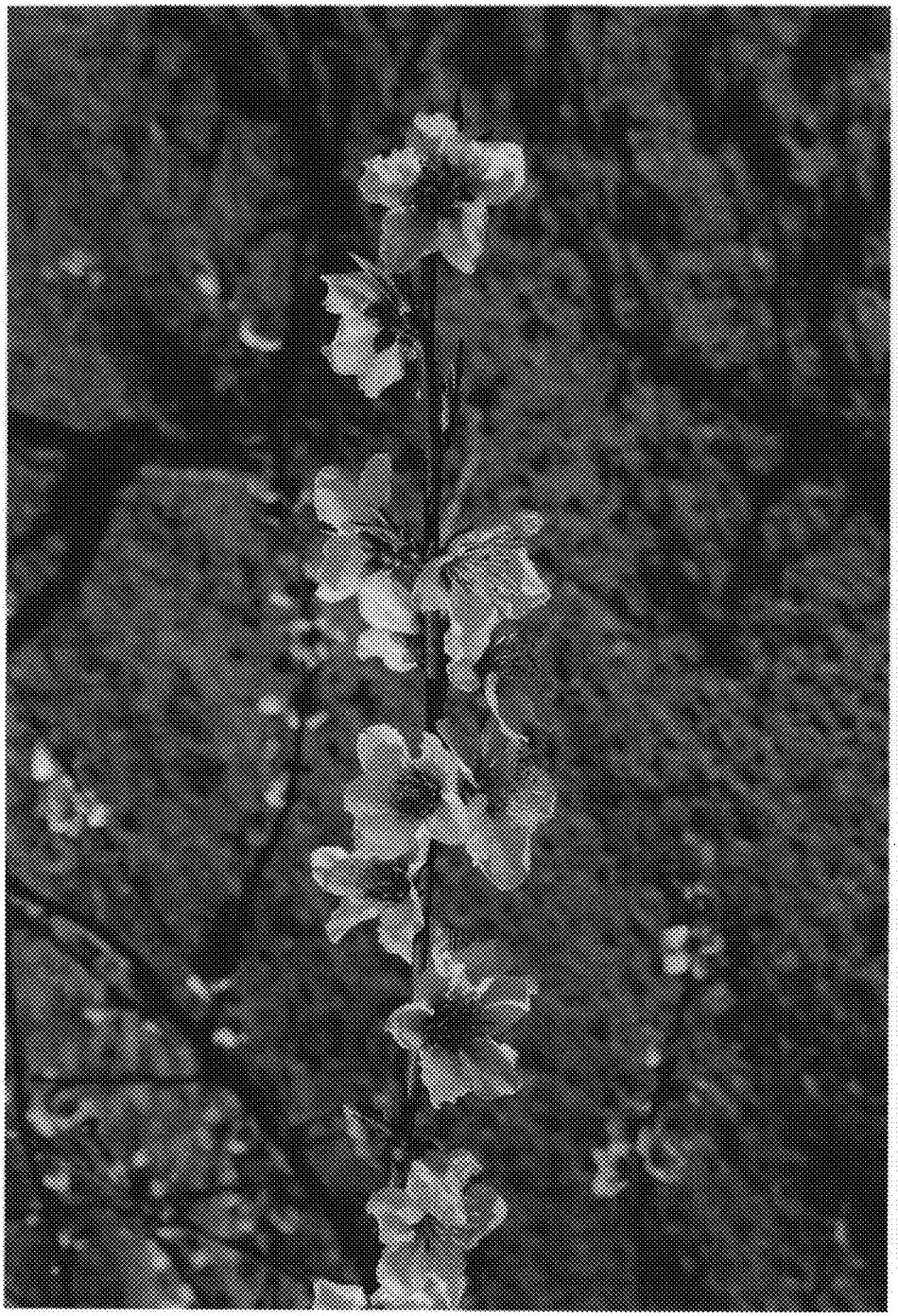
FIG. 6 shows a close up of a flowering branch of the new variety in situ.
Figure 7:
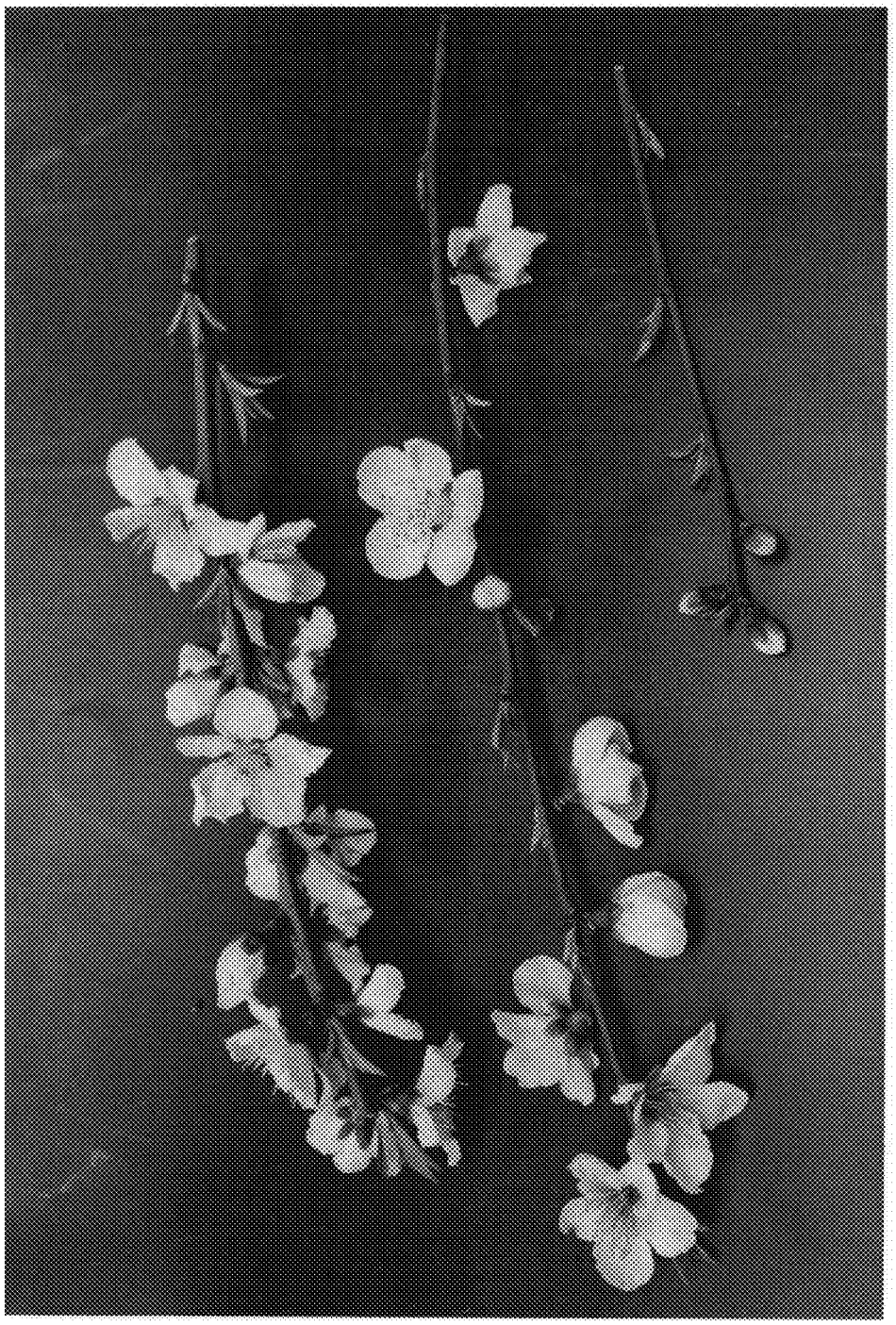
FIG. 7 shows a close up of several flowering branches removed from a tree of the new variety.

Referring more specifically to the pomological description of this new and distinct variety of peach tree, the following has been observed under the ecological conditions prevailing in the location of origin which is near Sanger, Calif. in the San Joaquin Valley of Central California. All major color code designations are by reference to the Dictionary of Color by Maerz & Paul, First Edition 1930. Common color names are also occasionally employed.

Tree:

*Size*.—Tree is similar in size and growth habit to 'Calara'. 8 ft×8 ft — small-medium size for peaches.

*Vigor*.—Moderate at second year of growth.

*Figure (form)*.—Upright and spreading with Tatura trellis system of training. Productivity is very good for tree in second year of growth. Regularity of bearing appears to be regular (i.e., every year, not in alternate years).

*Trunk size*.—Medium (diameter 9", 10" above soil level) — moderately rough. Color — Cub to Clove Manchu Sherry Brown+Rangoon — (15-C-1 to 15-C-12). Lenticels: Oval form, medium. Length: from 2-10 mm. Color: tan (11-G-4). Number: many.

*Branches*.—Size — Medium. Surface texture — slightly rough. a. Mature — Slightly Rough. b. Immature — Smooth. Color Code (one year or older) — bronze-umber (15-J-11). Color Code (immature) — Biscay Gr. (21-K-5). Three to four scaffold with lateral branches, at this stage of growth, being develop fruit wood and allow maximum sunlight for fruit colors. Diameter of scaffold branches taken at about two feet above soil level is 4-5 inches in circumference.

Leaves:

*Size*.—Medium to large.

*Length*.—81-175 mm.

*Width*.—16-42 mm.

*Shape*.—Lanceolate to nearly linear, leaf tip acuminate.

*Texture*.—Smooth.

*Color code*.—Upwardly disposed surface (upper side) — Art Gr. (22-L-7). Downwardly disposed surface (underside) — fern (21-H-6).

*Marginal form*.—Crenate to serrate, slightly undulate in larger leaves.

*Leaf base*.—Acute but oblique (asymmetrical).

*Leaf vein*.—Color Code: very pale green (18-H-4). Thickness: 0.5-1.5 mm.

*Glandular characteristics*.—Reniform — alternate. Color: cocoa turtle apache +sahara — (7-E-12). Size: 0.8-1 mm. Number: 2-4.

*Petiole*.—Size: Medium. Length: from 7-12 mm. Diameter: from 1-2 mm. Color Code: spring green (18-L-7).

*Stipules*.—Deciduous, only present in young leaves, in pairs at petiole base. Length — from 8-11 mm. Width — from 0.5-1 mm. Shape — linear. Color Code — bright green, 21-L-9.

Flowers:

*Flower buds*.—Hardy under typical central San Joaquin Valley climate condition. Size: dormant buds of average size. Length: from 10-14 mm. Form: ellipsoidal.

*Bud scales*.—Color — Piccaninny Perique+Otter — (8-E-11) or Mandalay Friar+ (8-L-12) and pubescent on surface.

*Generally*.—Showy type.

*Date of bloom*.—100% bloom as of approximately March 13 in a typical year, later than 'Calara'.

*Size*.—Generally medium to large.

*Diameter*.—When fully expanded 36-43 mm.

*Bloom quality*.—Abundant.

*Fragrance, slight*.—Typical peach.

*Petals*.—Size — medium to large. Length: 17 mm-22 mm. Width: 12 mm-20 mm. Form — broadly ovate. Number — five. Color — Damask (4-K-1) to very very light pink (41-B-1) at apex. Petal claws — broadly truncate. Width — 1 mm-1.5 mm. Length — 1 mm-1.5 mm. Petal margins — moderately undulated with somewhat rounded margins. Flower pedicel: very short 3-4 mm. Color — Courge Gr. (21-L-3). Surface — glabrous. Diameter — 1-2 mm.

*Sepals*.—Surface — pubescent. Size — medium to large. Form — ovate. Color — maroon (55-L-5) at base, to gray-green (21-E-2) along sepal lobe edges, with green color (21-K-7) inside of sepals. Number — five.

*Hypanthium*.—Outside color — bronze (56-L-5) at base and maroon (55-L-5) near base of sepals. Inside of hypanthium, color — near Navaho (10-D-12).

*Anthers*.—Size — average. Color — Chianti Antique Ruby+ (6-L-6).

*Pollen*.—present, Pyrethrum Y. (11-L-2).

*Stamen*.—8-15 mm. Number — 35-45.

*Filament*.—Color white (49-A-1) to light Persian Lilac (51-H-1).

*Position of stamens relative to petals*.—Same level.

*Pistil*.—Length — average 15 mm. Number — one. Color — light green (17-1-2) at the base, Touquet (4-B-8) at the top. Surface — Pubescent.

*Stigma*.—Color — yellow-green (20-L-1).

*Ovary*.—Pubescent, ovary densely covered with unbranched, multicellular trichomes.

*Position of stigma relative to anthers*.—Same level.

Fruit:

*Date of maturity*.—September $7^{th}$ to $21^{st}$ in a normal year.

*Size*.—Diameter Axial Plane: from 58-65 mm. Transverse in Suture Plane: from 66-74 mm. Transverse at Rt. Angle to Suture Plane: from 62-71 mm.

*Form*.—Uniform. Symmetrical or Asymmetrical: Shape of fruit is slightly asymmetrical.

*Suture*.—Shallow but with distinct Buccaneer (4-L-12) coloration from base to apex.

*Ventral surface*.—Uneven.

*Stem cavity*.—Width: from 5-11 mm. Depth: from 10-14 mm. Length: from 10-17 mm. Shape: Oval.

*Stem*.—Short. Diameter: from 2-4 mm.

*Apex*.—Slightly Rounded.

*Pistil point*.—Oblique.

*Skin*.—Thickness normal for peach, medium pubescence.

*Texture*.—Firm.

*Color code*.—Blush Color — deep pinkish orange (9-H-9 or 9-H-12). Ground Color — varies over 50% at axis, from yellow to CADMIUM Yp (9-L-1 or 9-L-8). Flesh Color — Golden Glow (9-L-6). Color at Surface of Pit Cavity — Flirt or India Red Arabian Red+Red Robbin — (2-K-9 or 7-L-6). Color of Pit Well — Brigand (2-J-11).

*Juice production*.—Moderate.

*Flavor*.—Good.

*Aroma*.—Good.

*Fruit sweetness*.—Medium.

*Fruit acidity*.—Medium.

*Fibers*.—Number — Few. Texture — Firm.

*Ripening*.—Even.

*Eating quality*.—Good.

*Stone*.—Attachment — Freestone. Fibers — Numerous, Short, slightly thick. Size — Medium. Length: from 33-38 mm. Width: from 23-25 mm. Diameter: from 18-20 mm.

*Form*.—Ovate.

*Apex*.—Sharply acute.

*Color code, when dry*.—Light brown to Brazil brown — (6-D-10 to 8-L-8).

*Base*.—Slightly Rounded.

*Sides*.—Unequal.

*Texture*.—Pitted.

*Ridges*.—On both sides of stone and narrowing towards apex; ridge on one side of the stone is much stronger (i.e., multiple ridges present on that side).

*Tendency to split*.—None evident externally, although there is always a deeper suture in the flesh on one side of the stem cavity.

*Use*.—Fresh Market; Freezer Peach.

*Shipping and quality*.—Very Good. Fruit retains firmness longer than some peaches. Like most peach trees, the new variety has winter hardiness, and is not susceptible to damage during the dormant season. The fruit and foliage of the new variety do not evidence any particular susceptibility to heat. The above description of this new variety of peach tree is based on the growing conditions prevailing near Sanger, California in the Central San Joaquin Valley of California, variations of the usual magnitude and characteristics may occur due to change in cultural factors, including irrigation, fertilization, primary climatic changes, etc.

What is claimed is:

1. A new and distinct variety of peach tree as described and illustrated which is somewhat similar to 'Calara' (U.S. Plant Pat. No. 15,496), from which it is distinguished by producing fruit having a freestone rather than a clingstone, that ripens at the beginning of the harvesting period of 'Calara', with good exterior coloration and very good eating quality which are mature for commercial harvesting and shipment approximately September 7-21 in a normal year.

* * * * *